(12) United States Patent
Dattolo et al.

(10) Patent No.: US 9,275,193 B2
(45) Date of Patent: Mar. 1, 2016

(54) PROCESSING SYSTEM AND METHOD

(75) Inventors: James Dattolo, Somerville, MA (US); Todd A. Ballantyne, Amherst, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 1022 days.

(21) Appl. No.: 12/205,679

(22) Filed: Sep. 5, 2008

(65) Prior Publication Data

US 2009/0069922 A1  Mar. 12, 2009

Related U.S. Application Data

(60) Provisional application No. 61/092,394, filed on Aug. 27, 2008, provisional application No. 60/970,494, filed on Sep. 6, 2007, provisional application No. 60/970,493, filed on Sep. 6, 2007, provisional application No. 60/970,495, filed on Sep. 6, 2007.

(51) Int. Cl.
*G05B 19/042* (2006.01)
*G06F 19/00* (2011.01)

(52) U.S. Cl.
CPC ........ *G06F 19/3456* (2013.01); *G05B 19/0428* (2013.01); *G06F 19/3475* (2013.01)

(58) Field of Classification Search
USPC .......... 700/97, 95, 239, 285; 705/15; 222/243
See application file for complete search history.

(56) References Cited

U.S. PATENT DOCUMENTS

| | | | |
|---|---|---|---|
| 2,982,895 A | 5/1961 | Exon | |
| 3,738,356 A | 6/1973 | Workman | |
| 4,014,319 A | 3/1977 | Favre | |
| 4,315,523 A | 2/1982 | Mahawili et al. | |
| 4,613,325 A | 9/1986 | Abrams | |
| 4,941,353 A | 7/1990 | Fukatsu et al. | |
| 5,350,082 A | 9/1994 | Kiriakides et al. | |
| 5,757,667 A | 5/1998 | Shannon et al. | |
| 6,600,882 B1 | 7/2003 | Applegate | |
| 6,640,650 B2 | 11/2003 | Matsuzawa et al. | |
| 6,689,410 B2 * | 2/2004 | Gerber | 426/565 |
| 6,789,067 B1 * | 9/2004 | Liebenow | 705/15 |
| 7,084,769 B2 | 8/2006 | Bauer et al. | |
| 7,232,059 B2 | 6/2007 | Peebles | |

(Continued)

FOREIGN PATENT DOCUMENTS

| | | |
|---|---|---|
| EP | 1783568 A1 | 5/2007 |
| JP | 2004093065 A | 3/2004 |

(Continued)

OTHER PUBLICATIONS

International Preliminary Report on Patentability, dated Mar. 18, 2010, received in international patent application No. PCT/US08/075473, 6 pgs.

(Continued)

*Primary Examiner* — Sean Shechtman
*Assistant Examiner* — Steven Garland
(74) *Attorney, Agent, or Firm* — Michelle Saquet Temple

(57) ABSTRACT

A method and computer program product for monitoring one or more processes occurring during a first portion of a multi-portion recipe being executed on a processing device to obtain data concerning at least of portion of the one or more processes. At least a portion of the data is stored. The availability of the at least a portion of the data is enabled to one or more processes occurring during a second portion of the multi-portion recipe.

3 Claims, 10 Drawing Sheets

(56) References Cited

U.S. PATENT DOCUMENTS

| | | | |
|---|---|---|---|
| 7,617,850 | B1 | 11/2009 | Dorney |
| 2002/0060226 | A1* | 5/2002 | Kameyama ................... 222/1 |
| 2003/0129286 | A1* | 7/2003 | Knepler ................... 426/231 |
| 2004/0261624 | A1 | 12/2004 | Lassota |
| 2005/0103799 | A1* | 5/2005 | Litterst et al. ................... 222/55 |
| 2006/0044192 | A1 | 3/2006 | Egbert |
| 2006/0081653 | A1 | 4/2006 | Boland et al. |
| 2007/0152829 | A1 | 7/2007 | Lindsay et al. |
| 2007/0205220 | A1* | 9/2007 | Rudick et al. ............. 222/129.4 |
| 2007/0294129 | A1* | 12/2007 | Froseth et al. ................... 705/10 |
| 2008/0008609 | A1 | 1/2008 | Pate et al. |
| 2008/0054837 | A1* | 3/2008 | Beavis et al. ................. 318/696 |
| 2008/0204347 | A1* | 8/2008 | Alvey et al. ................... 343/841 |

FOREIGN PATENT DOCUMENTS

| | | |
|---|---|---|
| WO | WO 01/83360 A2 | 11/2001 |
| WO | WO 2009/090354 A1 | 7/2009 |
| WO | WO2009/143289 A2 | 11/2009 |

OTHER PUBLICATIONS

International Preliminary Report on Patentability, dated Mar. 18, 2010, received in international patent application No. PCT/US08/075497, 8 pgs.

International Search Report with Written Opinion, dated Dec. 29, 2008, received in international patent application No. PCT/US08/75497, 10 pgs.

International Preliminary Report on Patentability with Written Opinion, dated Mar. 18, 2010, received in international patent application No. PCT/US08/75480, 9 pgs.

International Search Report and Written Opinion dated Mar. 6, 2012, received in international patent application No. PCT/US2009/055388, 12 pgs.

International Preliminary Report on Patentability dated Mar. 29, 2012, received in international patent application No. PCT/US2009/055388, 7 pgs.

International Preliminary Report on Patentability and Written Opinion dated Sep. 7, 2012, received in international patent application No. PCT/US2011/026274, 9 pgs.

European Search Report dated Sep. 24, 2012, received in European patent application No. 08829202.4, 6 pgs.

European Search Report dated Mar. 15, 2013, received in European patent application No. 08829307.1, 6 pgs.

International Search Report and Written Opinion dated Mar. 5, 2013, received in international patent application No. PCT/US2012/062215, 12 pgs.

Mini-Circuits, "*Segmented Magnetic Antennas for Near-field UHF RFID*" Microwave Journal, http://www.mwjournal.com/article.asp?HH_ID=AR_4597; 3 pgs, vol. 50, No. 6, Jun. 2007.

* cited by examiner

PROCESSING SYSTEM AND METHOD

RELATED APPLICATION(S)

This disclosure claims the priority of the following patent applications, each of which is herein incorporated by reference in its entirety: U.S. Provisional Application No. 61/092,394, entitled "PROCESSING SYSTEM AND METHOD" and filed 27 Aug. 2008; U.S. Provisional Application No. 60/970,494, entitled "VIRTUAL MANIFOLD SYSTEM AND METHOD" and filed 6 Sep. 2007; U.S. Provisional Application No. 60/970,493, entitled "FSM SYSTEM AND METHOD" and filed 6 Sep. 2007; and U.S. Provisional Application No. 60/970,495, entitled "VIRTUAL MACHINE SYSTEM AND METHOD" and filed 6 Sep. 2007.

TECHNICAL FIELD

This disclosure relates to processing systems and, more particularly, to processing systems that are used to generate products from a plurality of separate ingredients.

BACKGROUND

Processing systems may combine one or more ingredients to form a product. Unfortunately, such systems are often static in configuration and are only capable of generating a comparatively limited number of products. While such systems may be capable of being reconfigured to generate other products, such reconfiguration may require extensive changes to mechanical/electrical/software systems.

For example, in order to make a different product, new components may need to be added, such as e.g., new valves, lines, manifolds, and software subroutines. Such extensive modifications may be required due to existing devices/processes within the processing system being non-reconfigurable and having a single dedicated use, thus requiring that additional components be added to accomplish new tasks.

SUMMARY OF DISCLOSURE

In a first implementation, a method includes monitoring one or more processes occurring during a first portion of a multi-portion recipe being executed on a processing device to obtain data concerning at least of portion of the one or more processes. At least a portion of the data is stored. The availability of the at least a portion of the data is enabled to one or more processes occurring during a second portion of the multi-portion recipe.

One or more of the following features may be included. The first portion of a multi-portion recipe may be executed within a first manifold of the processing device. The first manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

The second portion of a multi-portion recipe may be executed within a second manifold of the processing device. The second manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

The data obtained may be chosen from the group consisting of: ingredient data and processing data. Enabling the availability of the at least a portion of the data may include routing the data to one or more processes occurring during the second portion of the multi-portion recipe.

Storing at least a portion of the data may include archiving the data in a nonvolatile memory system for subsequent diagnostic purposes. Storing at least a portion of the data includes temporarily writing the data to a volatile memory system.

The one or more processes monitored may be executed within a single manifold of the processing device. The one or more processes monitored may be representative of a single portion of a multi-portion procedure executed within a single manifold of the processing device.

In another implementation, a computer program product resides on a computer readable medium that has a plurality of instructions stored on it. When executed by a processor, the instructions cause the processor to perform operations including monitoring one or more processes occurring during a first portion of a multi-portion recipe being executed on a processing device to obtain data concerning at least of portion of the one or more processes. At least a portion of the data is stored. The availability of the at least a portion of the data is enabled to one or more processes occurring during a second portion of the multi-portion recipe.

One or more of the following features may be included. The first portion of a multi-portion recipe may be executed within a first manifold of the processing device. The first manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

The second portion of a multi-portion recipe may be executed within a second manifold of the processing device. The second manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

The data obtained may be chosen from the group consisting of: ingredient data and processing data. Enabling the availability of the at least a portion of the data may include routing the data to one or more processes occurring during the second portion of the multi-portion recipe.

Storing at least a portion of the data may include archiving the data in a nonvolatile memory system for subsequent diagnostic purposes. Storing at least a portion of the data includes temporarily writing the data to a volatile memory system.

The one or more processes monitored may be executed within a single manifold of the processing device. The one or more processes monitored may be representative of a single portion of a multi-portion procedure executed within a single manifold of the processing device.

In another implementation, a method includes receiving instructions to generate a product on a processing device. The instructions are processed to determine if the product is a multi-component product. If the product is a multi-component product, a first recipe is identified to produce a first component of the multi-component product and at least a second recipe is identified to produce at least a second component of the multi-component product. The first and second recipes are chosen from a plurality of available recipes. The first and second recipes are executed.

One or more of the following features may be included. The first recipe may be executed within a first manifold of the processing device. The first manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

The second recipe may be executed within a second manifold of the processing device. The second manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

In another implementation, a computer program product resides on a computer readable medium that has a plurality of instructions stored on it. When executed by a processor, the instructions cause the processor to perform operations including receiving instructions to generate a product on a processing device. The instructions are processed to determine if the product is a multi-component product. If the product is a multi-component product, a first recipe is identified to produce a first component of the multi-component product and at least a second recipe is identified to produce at least a second component of the multi-component product. The first and second recipes are chosen from a plurality of available recipes. The first and second recipes are executed.

One or more of the following features may be included. The first recipe may be executed within a first manifold of the processing device. The first manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

The second recipe may be executed within a second manifold of the processing device. The second manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

In another implementation, a process controller is configured to receive instructions to generate a product on a processing device. The instructions are processed to determine if the product is a multi-component product. If the product is a multi-component product, a first recipe is identified to produce a first component of the multi-component product and at least a second recipe is identified to produce at least a second component of the multi-component product. The first and second recipes are chosen from a plurality of available recipes. The first and second recipes are executed.

One or more of the following features may be included. The first recipe may be executed within a first manifold of the processing device. The first manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

The second recipe may be executed within a second manifold of the processing device. The second manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

In another implementation, a method includes receiving an indication of a product to be produced on a processing device. A recipe for the product is identified, wherein the recipe is chosen from a plurality of available recipes. The recipe is processed to parse the recipe into a plurality of discrete states and define one or more state transitions. At least one finite state machine is defined for the recipe using at least a portion of the plurality of discrete states.

One or more of the following features may be included. The recipe may be executed within a manifold of the processing device. The manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold. At least a portion of the plurality of discrete states may be sequential discrete states.

In another implementation, a computer program product resides on a computer readable medium that has a plurality of instructions stored on it. When executed by a processor, the instructions cause the processor to perform operations including receiving an indication of a product to be produced on a processing device. A recipe for the product is identified, wherein the recipe is chosen from a plurality of available recipes. The recipe is processed to parse the recipe into a plurality of discrete states and define one or more state transitions. At least one finite state machine is defined for the recipe using at least a portion of the plurality of discrete states.

One or more of the following features may be included. The recipe may be executed within a manifold of the processing device. The manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold. At least a portion of the plurality of discrete states may be sequential discrete states.

In another implementation, a method includes receiving an indication of a multi-component product to be produced on a processing device. The multi-component product includes a first product component, and at least a second product component. A first recipe is identified for the first product component. The first recipe is chosen from a plurality of available recipes. A second recipe is identified for the second product component. The second recipe is chosen from the plurality of available recipes. The first and second recipes are processed to parse the first and second recipes into a plurality of discrete states and define one or more state transitions. A first finite state machine is defined for the first recipe using at least a first portion of the plurality of discrete states. A second finite state machine is defined for the second recipe using at least a second portion of the plurality of discrete states.

One or more of the following features may be included. The first product component may be produced within a first manifold of the processing device. The first manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

The second product component may be produced within a second manifold of the processing device. The second manifold may be chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold. At least a portion of the plurality of discrete states may be sequential discrete states.

The details of one or more implementations are set forth in the accompanying drawings and the description below. Other features and advantages will become apparent from the description, the drawings and the claims.

BRIEF DESCRIPTION OF THE DRAWINGS

These and other features and advantages of the present invention will be better understood by reading the following detailed description, taken together with the drawings wherein.

Like reference symbols in the various drawings indicate like elements.

DETAILED DESCRIPTION OF EXEMPLARY EMBODIMENTS

Figure 1:
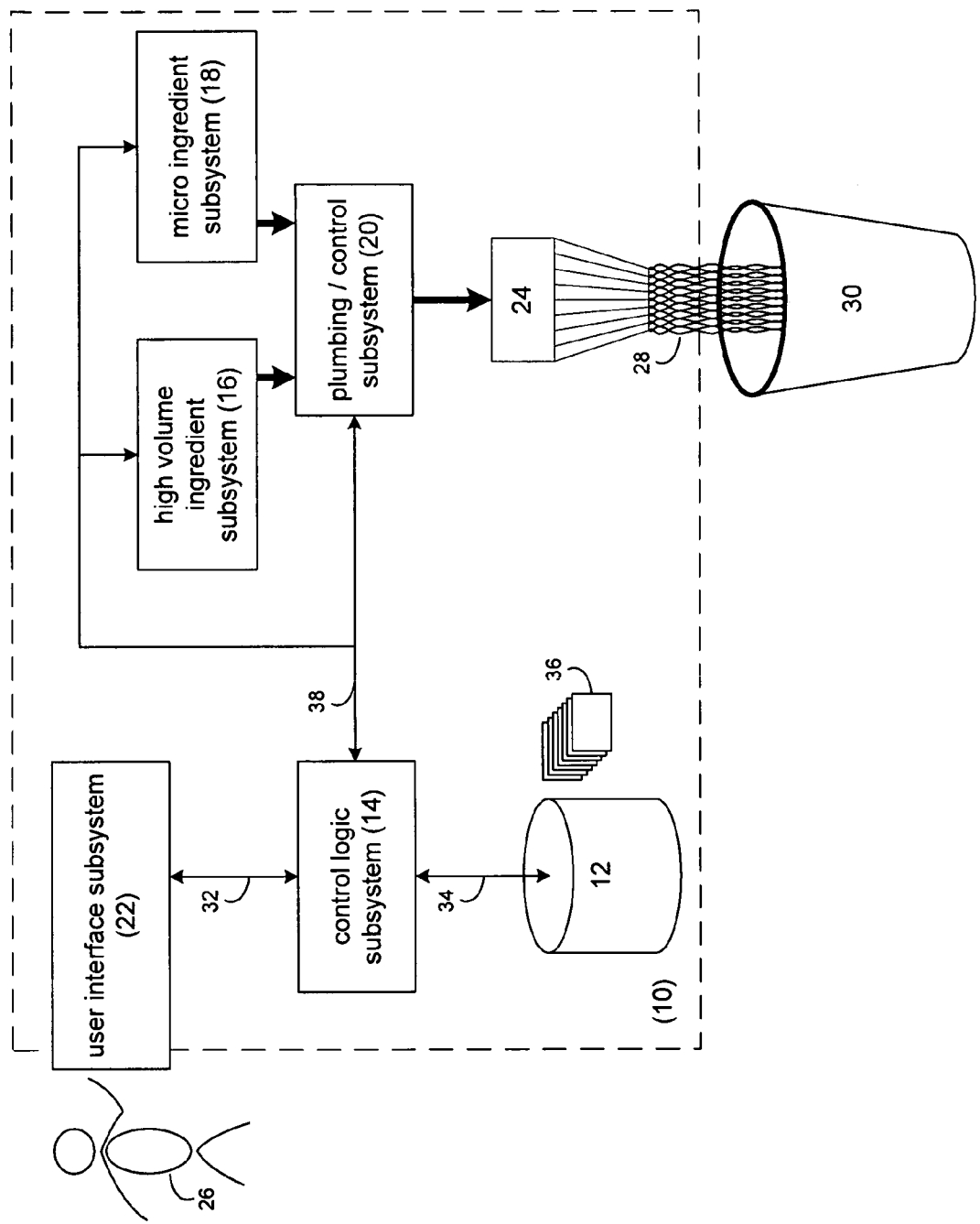
FIG. 1 is a diagrammatic view of one embodiment of a processing system.

Described herein is a product dispensing system. The system includes one or more modular components, also termed "subsystems". Although exemplary systems are described herein, in various embodiments, the product dispensing system may include one or more of the subsystems described, but the product dispensing system is not limited to only one or more of the subsystems described herein. Thus, in some embodiments, additional subsystems may be used in the product dispensing system.

The following disclosure will discuss the interaction and cooperation of various electrical components, mechanical components, electromechanical components, and software processes (i.e., "subsystems") that allow for the mixing and processing of various ingredients to form a product. Examples of such products may include but are not limited to: dairy-based products (e.g., milkshakes, floats, malts, frappes); coffee-based products (e.g., coffee, cappuccino, espresso); soda-based products (e.g., floats, soda w/fruit juice); tea-based products (e.g., iced tea, sweet tea, hot tea); water-based products (e.g., spring water, flavored spring water, spring water w/vitamins, high-electrolyte drinks, high-carbohydrate drinks); solid-based products (e.g., trail mix, granola-based products, mixed nuts, cereal products, mixed grain products); medicinal products (e.g., infusible medicants, injectable medicants, ingestible medicants, dialysates); alcohol-based products (e.g., mixed drinks, wine spritzers, soda-based alcoholic drinks, water-based alcoholic drinks, beer with flavor "shots"); industrial products (e.g., solvents, paints, lubricants, stains); and health/beauty aid products (e.g., shampoos, cosmetics, soaps, hair conditioners, skin treatments, topical ointments).

The products may be produced using one or more "ingredients". Ingredients may include one or more fluids, powders, solids or gases. The fluids, powders, solids, and/or gases may be reconstituted or diluted within the context of processing and dispensing. The products may be a fluid, solid, powder or gas.

The various ingredients may be referred to as "macroingredients", "microingredients", or "large volume microingredients". One or more of the ingredients used may be contained within a housing, i.e., part of a product dispensing machine. However, one or more of the ingredients may be stored or produced outside the machine. For example, in some embodiments, water (in various qualities) or other ingredients used in high volume may be stored outside of the machine (for example, in some embodiments, high fructose corn syrup may be stored outside the machine), while other ingredients, for example, ingredients in powder form, concentrated ingredients, nutraceuticals, pharmaceuticals and/or gas cylinders may be stored within the machine itself.

Various combinations of the above-referenced electrical components, mechanical components, electromechanical components, and software processes are discussed below. While combinations are described below that disclose e.g., the production of beverages and medicinal products (e.g., dialysates) using various subsystems, this is not intended to be a limitation of this disclosure, rather, exemplary embodiments of ways in which the subsystems may work together to create/dispense a product. Specifically, the electrical components, mechanical components, electromechanical components, and software processes (each of which will be discussed below in greater detail) may be used to produce any of the above-referenced products or any other products similar thereto.

Referring to FIG. 1, there is shown a generalized-view of processing system 10 that is shown to include a plurality of subsystems namely: storage subsystem 12, control logic subsystem 14, high volume ingredient subsystem 16, microingredient subsystem 18, plumbing/control subsystem 20, user interface subsystem 22, and nozzle 24. Each of the above describes subsystems 12, 14, 16, 18, 20, 22 will be described below in greater detail.

During use of processing system 10, user 26 may select a particular product 28 for dispensing (into container 30) using user interface subsystem 22. Via user interface subsystem 22, user 26 may select one or more options for inclusion within such product. For example, options may include but are not limited to the addition of one or more ingredients. In one exemplary embodiment, the system is a system for dispensing a beverage. In this embodiment, the use may select various flavorings (e.g. including but not limited to lemon flavoring, lime flavoring, chocolate flavoring, and vanilla flavoring) into a beverage; the addition of one or more nutraceuticals (e.g. including but not limited to Vitamin A, Vitamin C, Vitamin D, Vitamin E, Vitamin $B_6$, Vitamin $B_{12}$, and Zinc) into a beverage; the addition of one or more other beverages (e.g. including but not limited to coffee, milk, lemonade, and iced tea) into a beverage; and the addition of one or more food products (e.g. ice cream, yogurt) into a beverage.

Once user 26 makes the appropriate selections, via user interface subsystem 22, user interface subsystem 22 may send the appropriate data signals (via data bus 32) to control logic subsystem 14. Control logic subsystem 14 may process these data signals and may retrieve (via data bus 34) one or more recipes chosen from plurality of recipes 36 maintained on storage subsystem 12. The term "recipe" refers to instructions for processing/creating the requested product. Upon retrieving the recipe(s) from storage subsystem 12, control logic subsystem 14 may process the recipe(s) and provide the appropriate control signals (via data bus 38) to e.g. high volume ingredient subsystem 16 microingredient subsystem 18 (and, in some embodiments, large volume microingredients, not shown, which may be included in the description with respect to microingredients with respect to processing. With respect to the subsystems for dispensing these large volume microingredients, in some embodiments, an alternate assembly from the microingredient assembly, may be used to dispense these large volume microingredients), and plumbing/control subsystem 20, resulting in the production of product 28 (which is dispensed into container 30).

Figure 2:
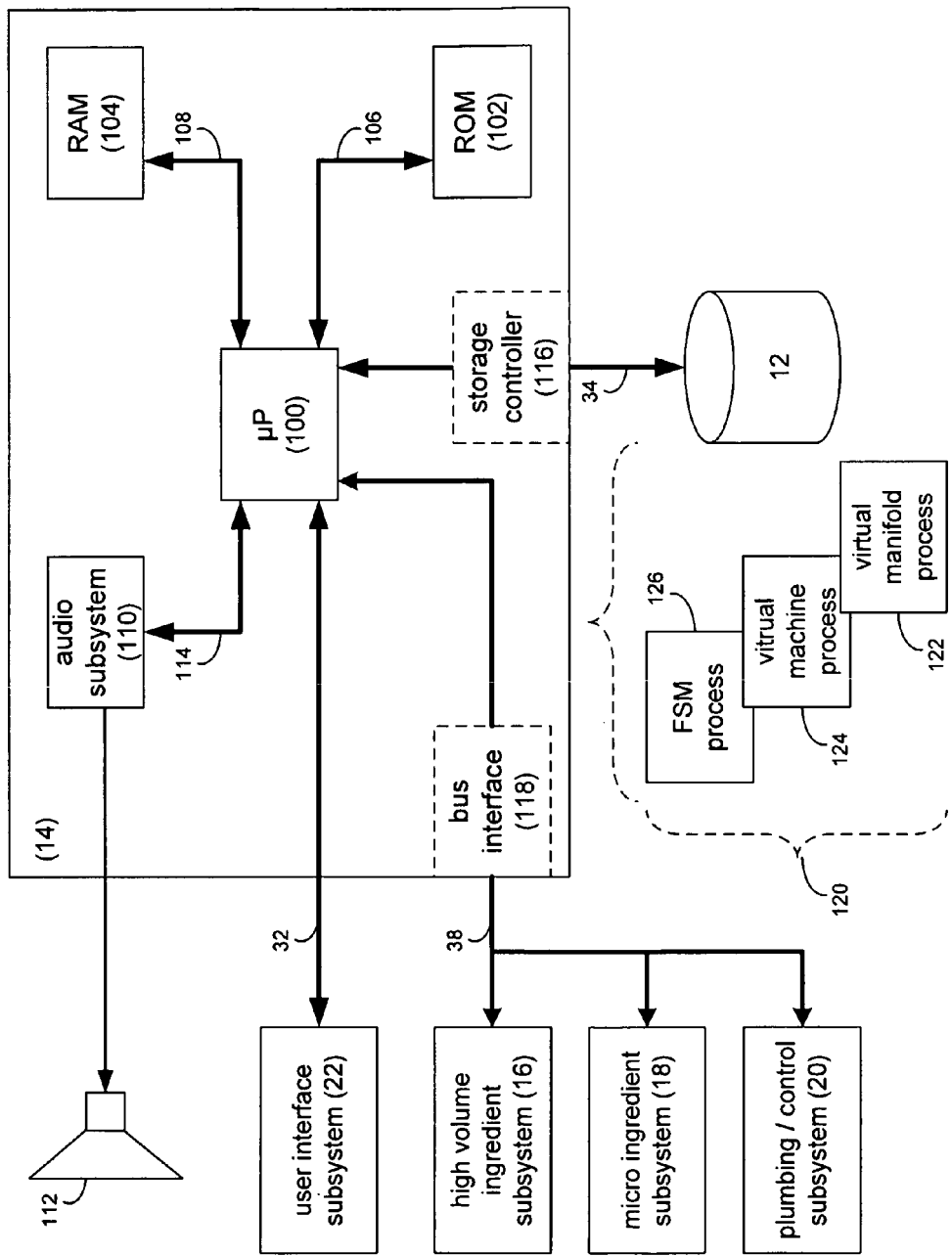
FIG. 2 is a diagrammatic view of one embodiment of a control logic subsystem included within the processing system of FIG. 1.

Referring also to FIG. 2, a diagrammatic view of control logic subsystem 14 is shown. Control logic subsystem 14 may include microprocessor 100 (e.g., an ARM™ microprocessor produced by Intel Corporation of Santa Clara, Calif.), non-volatile memory (e.g. read only memory 102), and volatile memory (e.g. random access memory 104); each of which may be interconnected via one or more data/system buses 106, 108. As discussed above, user interface subsystem 22 may be coupled to control logic subsystem 14 via data bus 32.

Control logic subsystem 14 may also include an audio subsystem 110 for providing e.g. an analog audio signal to speaker 112, which may be incorporated into processing system 10. Audio subsystem 110 may be coupled to microprocessor 100 via data/system bus 114.

Control logic subsystem 14 may execute an operating system, examples of which may include but are not limited to Microsoft Windows CE™, Redhat Linux™, Palm OS™, or a device-specific (i.e., custom) operating system.

The instruction sets and subroutines of the above-described operating system, which may be stored on storage subsystem 12, may be executed by one or more processors (e.g. microprocessor 100) and one or more memory architectures (e.g. read-only memory 102 and/or random access memory 104) incorporated into control logic subsystem 14.

Storage subsystem 12 may include, for example, a hard disk drive, an optical drive, a random access memory (RAM), a read-only memory (ROM), a CF (i.e., compact flash) card, an SD (i.e., secure digital) card, a SmartMedia card, a Memory Stick, and a MultiMedia card, for example.

As discussed above, storage subsystem 12 may be coupled to control logic subsystem 14 via data bus 34. Control logic subsystem 14 may also include storage controller 116 (shown in phantom) for converting signals provided by microprocessor 100 into a format usable by storage system 12. Further, storage controller 116 may convert signals provided by storage subsystem 12 into a format usable by microprocessor 100. In some embodiments, an Ethernet connection may also be included.

As discussed above, high-volume ingredient subsystem 16 (also referred to herein as "macroingredients"), microingredient subsystem 18 and/or plumbing/control subsystem 20 may be coupled to control logic subsystem 14 via data bus 38. Control logic subsystem 14 may include bus interface 118 (shown in phantom) for converting signals provided by microprocessor 100 into a format usable by high-volume ingredient subsystem 16, microingredient subsystem 18 and/or plumbing/control subsystem 20. Further, bus interface 118 may convert signals provided by high-volume ingredient subsystem 16, microingredient subsystem 18 and/or plumbing/control subsystem 20 into a format usable by microprocessor 100.

As will be discussed below in greater detail, control logic subsystem 14 may execute one or more control processes 120 that may control the operation of processing system 10. The instruction sets and subroutines of control processes 120, which may be stored on storage subsystem 12, may be executed by one or more processors (e.g. microprocessor 100) and one or more memory architectures (e.g. read-only memory 102 and/or random access memory 104) incorporated into control logic subsystem 14.

Figure 3:
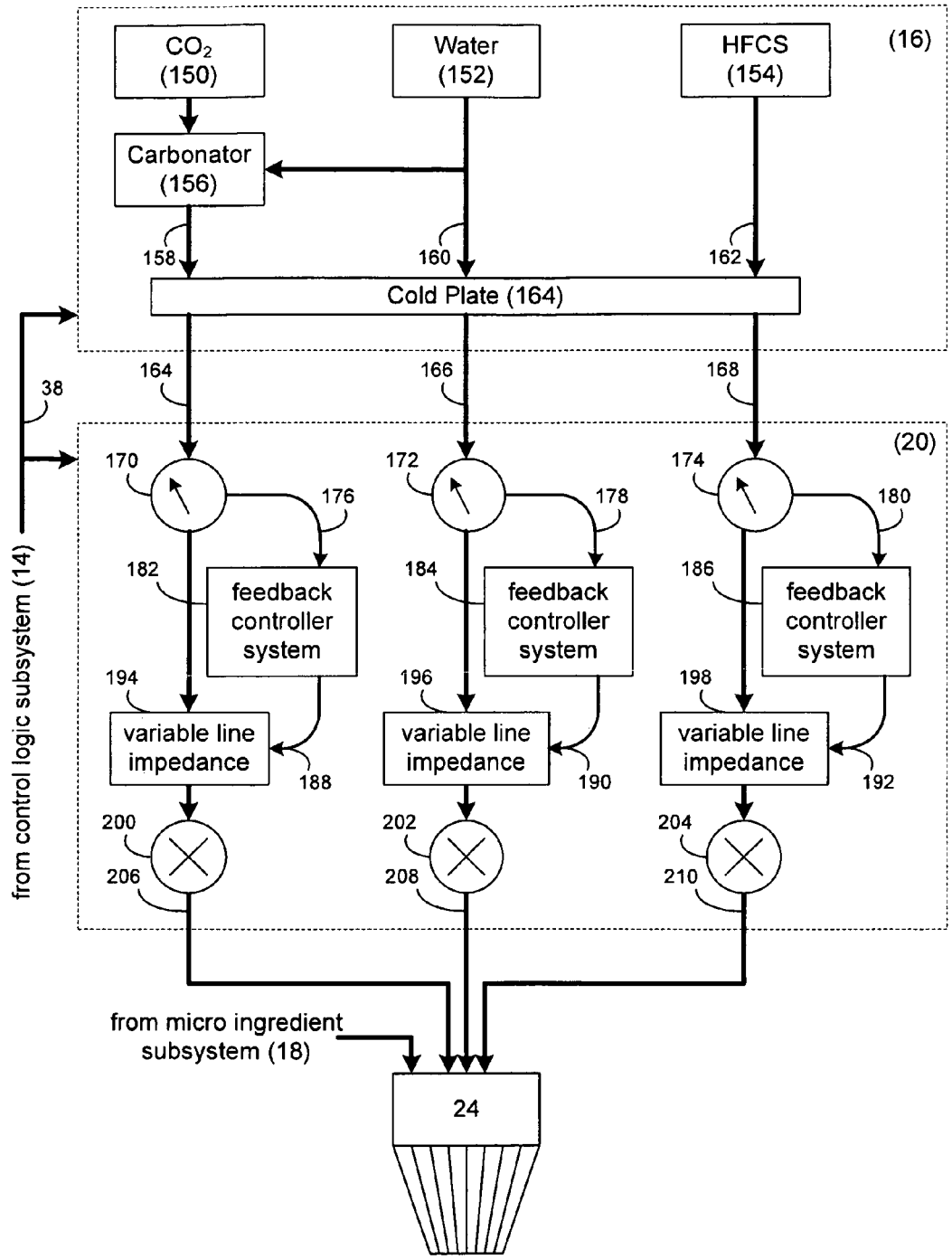
FIG. 3 is a diagrammatic view of one embodiment of a high volume ingredient subsystem included within the processing system of FIG. 1.

Referring also to FIG. 3, a diagrammatic view of high-volume ingredient subsystem 16 and plumbing/control subsystem 20 are shown. High-volume ingredient subsystem 16 may include containers for housing consumables that are used at a rapid rate when making beverage 28. For example, high-volume ingredient subsystem 16 may include carbon dioxide supply 150, water supply 152, and high fructose corn syrup supply 154. The high-volume ingredients, in some embodiments, may be located within close proximity to the other subsystems. An example of carbon dioxide supply 150 may include but is not limited to a tank (not shown) of compressed, gaseous carbon dioxide. An example of water supply 152 may include but is not limited to a municipal water supply (not shown), a distilled water supply, a filtered water supply, a reverse-osmosis ("RO") water supply or other desired water supply. An example of high fructose corn syrup supply 154 may include but is not limited to one or more tank(s) (not shown) of highly-concentrated, high fructose corn syrup, or one or more bag-in-box packages of high-fructose corn syrup.

High-volume, ingredient subsystem 16 may include a carbonator 156 for generating carbonated water from carbon dioxide gas (provided by carbon dioxide supply 150) and water (provided by water supply 152). Carbonated water 158, water 160 and high fructose corn syrup 162 may be provided to cold plate assembly 164 e.g., in embodiments where a product is being dispensed in which it may be desired to be cooled. In some embodiments, the cold plate assembly may not be included as part of the dispensing systems or may be bi-passed. Cold plate assembly 164 may be designed to chill carbonated water 158, water 160, and high fructose corn syrup 162 down to a desired serving temperature (e.g. 40° F.).

While a single cold plate 164 is shown to chill carbonated water 158, water 160, and high fructose corn syrup 162, this is for illustrative purposes only and is not intended to be a limitation of disclosure, as other configurations are possible. For example, an individual cold plate may be used to chill each of carbonated water 158, water 160 and high fructose corn syrup 162. Once chilled, chilled carbonated water 164, chilled water 166, and chilled high fructose corn syrup 168 may be provided to plumbing/control subsystem 20. And in still other embodiments, a cold plate may not be included. In some embodiments, at least one hot plate may be included.

Although the plumbing is depicted as having the order shown, in some embodiments, this order is not used. For example, the flow control modules described herein may be configured in a different order, i.e., flow measuring device, binary valve and then variable line impendence.

For descriptive purposes, the system will be described below with reference to using the system to dispense soft drinks as a product, i.e., the macroingredients/high-volume ingredients described will include high-fructose corn syrup, carbonated water and water. However, in other embodiments of the dispensing system, the macroingredients themselves, and the number of macroingredients, may vary.

For illustrative purposes, plumbing/control subsystem 20 is shown to include three flow measuring devices 170, 172, 174, which measure the volume of chilled carbonated water 164, chilled water 166 and chilled high fructose corn syrup 168 (respectively). Flow measuring devices 170, 172, 174 may provide feedback signals 176, 178, 180 (respectively) to feedback controller systems 182, 184, 186 (respectively). Feedback controller systems 182, 184, 186 (which will be discussed below in greater detail) may compare flow feedback signals 176, 178, 180 to the desired flow volume (as defined for each of chilled carbonated water 164, chilled water 166 and chilled high fructose corn syrup 168; respectively). Upon processing flow feedback signals 176, 178, 180, feedback controller systems 182, 184, 186 (respectively) may generate flow control signals 188, 190, 192 (respectively) that may be provided to variable line impedances 194, 196, 198 (respectively). Examples of variable line impedance 194, 196, 198 are disclosed and claimed in U.S. Pat. No. 5,755,683 (which is herein incorporated by reference in its entirety), U.S. patent application Ser. No. 11/559,792 (which is herein incorporated by reference in its entirety) and U.S. patent application Ser. No. 11/851,276 (which is herein incorporated by reference in its entirety). Variable line impedances 194, 196, 198 may regulate the flow of chilled carbonated water 164, chilled water 166 and chilled high fructose corn syrup 168 passing through lines 206, 208, 210 (respectively), which are provided to nozzle 24 and (subsequently) container 30. However, additional embodiments of the variable line impedances are described herein.

Lines 206, 208, 210 may additionally include solenoid valves 200, 202, 204 (respectively) for preventing the flow of fluid through lines 206, 208, 210 during times when fluid flow is not desired/required (e.g. during shipping, maintenance procedures, and downtime).

As discussed above, FIG. 3 merely provides an illustrative view of plumbing/control subsystem 20. Accordingly, the manner in which plumbing/control subsystem 20 is illustrated is not intended to be a limitation of this disclosure, as other configurations are possible. For example, some or all of the functionality of feedback controller systems 182, 184, 186 may be incorporated into control logic subsystem 14.

Figure 4:
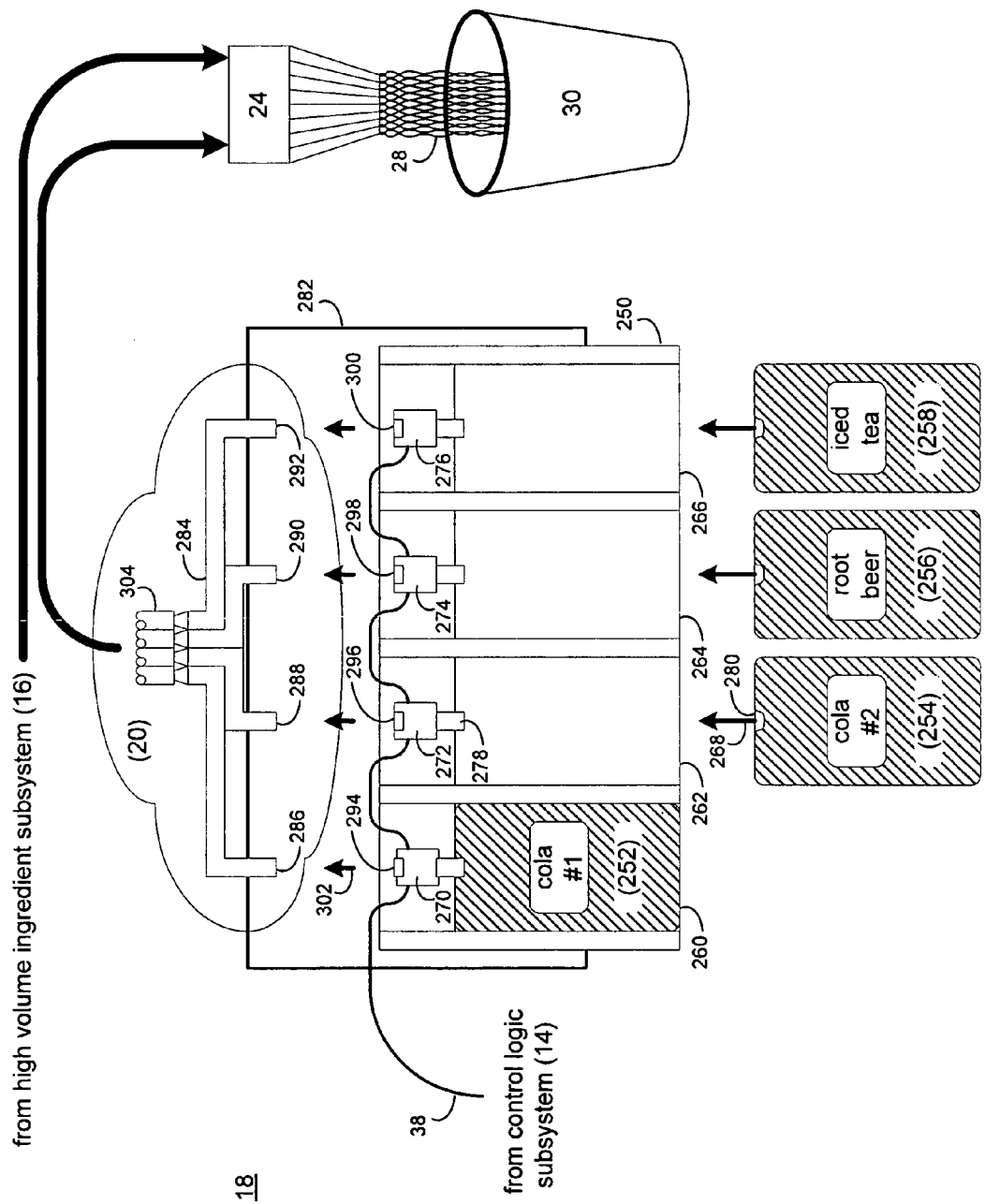
FIG. 4 is a diagrammatic view of one embodiment of a micro ingredient subsystem included within the processing system of FIG. 1.

Referring also to FIG. 4, a diagrammatic top-view of microingredient subsystem 18 and plumbing/control subsystem 20 is shown. Microingredient subsystem 18 may include product module assembly 250, which may be configured to releasably engage one or more product containers 252, 254, 256, 258, which may be configured to hold microingredients for use when making product 28. The microingredients may be substrates that may be used in making the product Examples of such micro ingredients/substrates may include but are not limited to a first portion of a soft drink flavoring, a second portion of a soft drink flavoring, coffee flavoring, nutraceuticals, and pharmaceuticals; and may be fluids, powders or solids. However and for illustrative purposes, the description below refers to microingredients that are fluids. In some embodiments, the microingredients may be powders or solids. Where a microingredient is a powder, the system may include an additional subsystem for metering the powder and/or reconstituting the powder (although, as described in examples below, where the microingredient is a powder, the powder may be reconstituted as part of the methods of mixing the product).

Product module assembly 250 may include a plurality of slot assemblies 260, 262, 264, 266 configured to releasably engage plurality of product containers 252, 254, 256, 258. In this particular example, product module assembly 250 is shown to include four slot assemblies (namely slots 260, 262, 264, 266) and, therefore, may be referred to as a quad product module assembly. When positioning one or more of product containers 252, 254, 256, 258 within product module assembly 250, a product container (e.g. product container 254) may be slid into a slot assembly (e.g. slot assembly 262) in the direction of arrow 268. Although as shown herein, in the exemplary embodiment, a "quad product module" assembly is described, in other embodiments, more or less product may be contained within a module assembly. Depending on the product being dispensed by the dispensing system, the numbers of product containers may vary. Thus, the numbers of product contained within any module assembly may be application specific, and may be selected to satisfy any desired characteristic of the system, including, but not limited to, efficiency, necessity and/or function of the system.

For illustrative purposes, each slot assembly of product module assembly 250 is shown to include a pump assembly. For example, slot assembly 252 shown to include pump assembly 270; slot assembly 262 shown to include pump assembly 272; slot assembly 264 is shown to include pump assembly 274; and slot assembly 266 is shown to include pump assembly 276.

Each of pump assemblies 270, 272, 274, 276 may include an inlet port for releasably engaging a product orifice included within the product container. For example, pump assembly 272 a shown to include inlet port 278 that is configured to releasably engage container orifice 280 included within product container 254. Inlet port 278 and/or product orifice 280 may include one or more sealing assemblies (e.g., one or more o-rings/luer fittings; not shown) to facilitate a leakproof seal.

An example of one or more of pump assembly 270, 272, 274, 276 may include but is not limited to a solenoid piston pump assembly that provides a defined and consistent amount of fluid each time that one or more of pump assemblies 270, 272, 274, 276 are energized. In one embodiment, such pumps are available from ULKA Costruzioni Elettromeccaniche S.p.A. of Pavia, Italy. For example, each time a pump assembly (e.g. pump assembly 274) is energized by control logic subsystem 14 via data bus 38, the pump assembly may provide a calibrated volume of the root beer flavoring included within product container 256. Again, for illustrative purposes only, the microingredients are fluids in this section of the description.

Other examples of pump assemblies 270, 272, 274, 276 and various pumping techniques are described in U.S. Pat. No. 4,808,161 (which is herein incorporated by reference in its entirety); U.S. Pat. No. 4,826,482 (which is herein incorporated by reference in its entirety); U.S. Pat. No. 4,976,162 (which is herein incorporated by reference in its entirety); U.S. Pat. No. 5,088,515 (which is herein incorporated by reference in its entirety); and U.S. Pat. No. 5,350,357 (which is herein incorporated by reference in its entirety). In some embodiments, the pump assembly may be any of the pump assemblies and may use any of the pump techniques described in U.S. Pat. No. 5,421,823 (which is herein incorporated by reference in its entirety).

The above-cited references describe non-limiting examples of pneumatically actuated membrane-based pumps that may be used to pump fluids. A pump assembly based on a pneumatically actuated membrane may be advantageous, for one or more reasons, including but not limited to, ability to deliver quantities, for example, microliter quantities, of fluids of various compositions reliably and precisely over a large number of duty cycles; and/or because the pneumatically actuated pump may require less electrical power because it may use pneumatic power, for example, from a carbon dioxide source. Additionally, a membrane-based pump may not require a dynamic seal, in which the surface moves with respect to the seal. Vibratory pumps such as those manufactured by ULKA generally require the use of dynamic elastomeric seals, which may fail over time for example, after exposure to certain types of fluids and/or wear. In some embodiments, pneumatically-actuated membrane-based pumps may be more reliable, cost effective and easier to calibrate than other pumps. They may also produce less noise, generate less heat and consume less power than other pumps.

Product module assembly 250 may be configured to releasably engage bracket assembly 282. Bracket assembly 282 may be a portion of (and rigidly fixed within) processing system 10. Although referred to herein as a "bracket assembly", the assembly may vary in other embodiments. The bracket assembly serves to secure the product module assembly 282 in a desired location. An example of bracket assembly 282 may include but is not limited to a shelf within processing system 10 that is configured to releasably engage product module 250. For example, product module 250 may include a engagement device (e.g. a clip assembly, a slot assembly, a latch assembly, a pin assembly; not shown) that is configured to releasably engage a complementary device that is incorporated into bracket assembly 282.

Plumbing/control subsystem 20 may include manifold assembly 284 that may be rigidly affixed to bracket assembly 282. Manifold assembly 284 may be configured to include a plurality of inlet ports 286, 288, 290, 292 that are configured to releasably engage a pump orifice (e.g. pump orifices 294, 296, 298, 300) incorporated into each of pump assemblies 270, 272, 274, 276. When positioning product module 250 on bracket assembly 282, product module 250 may be moved in the direction of the arrow 302, thus allowing for inlet ports 286, 288, 290, 292 to releasably engage pump orifices 294, 296, 298, 300. Inlet ports 286, 288, 290, 292 and/or pump orifices 294, 296, 298, 300 may include one or more O-ring or other sealing assemblies as described above (not shown) to facilitate a leakproof seal.

Manifold assembly 284 may be configured to engage tubing bundle 304, which may be plumbed (either directly or indirectly) to nozzle 24. As discussed above, high-volume ingredient subsystem 16 also provides fluids in the form of, in at least one embodiment, chilled carbonated water 164, chilled water 166 and/or chilled high fructose corn syrup 168 (either directly or indirectly) to nozzle 24. Accordingly, as control logic subsystem 14 may regulate (in this particular example) the specific quantities of the various high-volume ingredients e.g. chilled carbonated water 164, chilled water 166, chilled high fructose corn syrup 168 and the quantities of the various micro ingredients (e.g. a first substrate (i.e., flavoring), a second substrate (i.e., a nutraceutical), and a third substrate (i.e., a pharmaceutical), control logic subsystem 14 may accurately control the makeup of product 28.

Although FIG. 4 depicts only one nozzle 24, in various other embodiments, multiple nozzles may be included. In some embodiments, more than one container 30 may receive product dispensed from the system via e.g., more than one set of tubing bundles. Thus, in some embodiments, the dispensing system may be configured such that one or more users may request one or more products to be dispensed concurrently.

Figure 5:
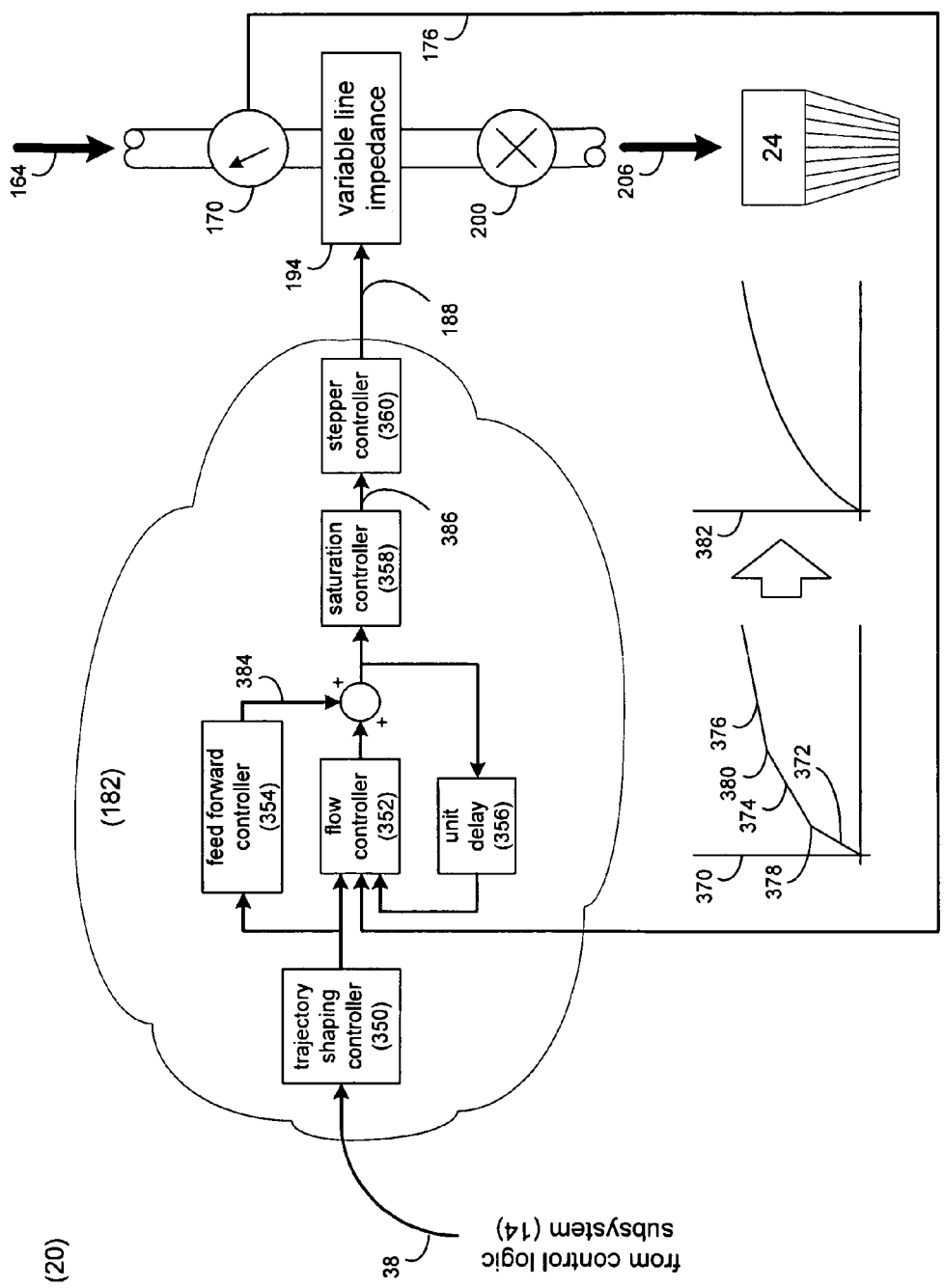
FIG. 5 is a diagrammatic view of one embodiment of a plumbing/control subsystem included within the processing system of FIG. 1.

Referring also to FIG. 5, a diagrammatic view of plumbing/control subsystem 20 is shown. While the plumbing/control subsystem described below concerns the plumbing/control system used to control the quantity of chilled carbonated water 164 being added to product 28, this is for illustrative purposes only and is not intended to be a limitation of this disclosure, as other configurations are also possible. For example, the plumbing/control subsystem described below may also be used to control e.g., the quantity of chilled water 166 and/or chilled high fructose corn syrup 168 being added to product 28.

As discussed above, plumbing/control subsystem 20 may include feedback controller system 182 that receives flow feedback signal 176 from flow measuring device 170. Feedback controller system 182 may compare flow feedback signal 176 to the desired flow volume (as defined by control logic subsystem 14 via data bus 38). Upon processing flow feedback signal 176, feedback controller system 182 may generate flow control signal 188 that may be provided to variable line impedance 194.

Feedback controller system 182 may include trajectory shaping controller 350, flow regulator 352, feed forward controller 354, unit delay 356, saturation controller 358, and stepper controller 360, each of which will be discussed below in greater detail.

Trajectory shaping controller 350 may be configured to receive a control signal from control logic subsystem 14 via data bus 38. This control signal may define a trajectory for the manner in which plumbing/control subsystem 20 is supposed to deliver fluid (in the case, chilled carbonated water 164) for use in product 28. However, the trajectory provided by control logic subsystem 14 may need to be modified prior to being processed by e.g., flow controller 352. For example, control systems tend to have a difficult time processing control curves that are made up of a plurality of linear line segments (i.e., that include step changes). For example, flow regulator 352 may have difficulty processing control curve 370, as it consists of three distinct linear segments, namely segments 372, 374, 376. Accordingly, at the transition points (e.g., transition points 378, 380), flow controller 352 specifically (and plumbing/control subsystem 20 generally) would be required to instantaneously change from a first flow rate to a second flow rate. Therefore, trajectory shaping controller 350 may filter control curve 30 to form smoothed control curve 382 that is more easily processed by flow controller 352 specifically (and plumbing/control subsystem 20 generally), as an instantaneous transition from a first flow rate to a second flow rate is no longer required.

Additionally, trajectory shaping controller 350 may allow for the pre-fill wetting and post-fill rinsing of nozzle 24. In some embodiments and/or for some recipes, one or more ingredients may present problems for nozzle 24 if the ingredient (referred to herein as "dirty ingredients") contacts nozzle 24 directly i.e., in the form in which it is stored. In some embodiments, nozzle 24 may be pre-fill wetted with a "pre-fill" ingredient e.g., water, so as to prevent the direct contact of these "dirty ingredients" with nozzle 24. Nozzle 24 may then be post-fill rinsed with a "post-wash ingredient" e.g., water.

Specifically, in the event that nozzle 24 is pre-fill wetted with e.g., 10 mL of water (or any "pre-fill" ingredient), and/or post-fill rinsed with e.g., 10 mL of water (or any "post-wash" ingredient), once the adding of the dirty ingredient has stopped, trajectory shaping controller 350 may offset the pre-wash ingredient added during the pre-fill wetting and/or post-fill rinsing by providing an additional quantity of dirty ingredient during the fill process. Specifically, as container 30 is being filled with product 28, the pre-fill rinse water or "pre-wash" may result in product 28 being initially underconcentrated with a the dirty ingredient, Trajectory shaping controller 350 may then add dirty ingredient at a higher-thanneeded flow rate, resulting in product 28 transitioning from "under-concentrated" to "appropriately concentrated" to "over-concentrated", or present in a concentration higher than that which is called for by the particular recipe. However, once the appropriate amount of dirty ingredient has been added, the post-fill rinse process may add additional water, or another appropriate "post-wash ingredient", resulting in product 28 once again becoming "appropriately-concentrated" with the dirty ingredient.

Flow controller 352 may be configured as a proportional-integral (PI) loop controller. Flow controller 352 may perform the comparison and processing that was generally described above as being performed by feedback controller system 182. For example, flow controller 352 may be configured to receive feedback signal 176 from flow measuring device 170. Flow controller 352 may compare flow feedback signal 176 to the desired flow volume (as defined by control logic subsystem 14 and modified by trajectory shaping controller 350). Upon processing flow feedback signal 176, flow controller 352 may generate flow control signal 188 that may be provided to variable line impedance 194.

Feed forward controller 354 may provide an "best guess" estimate concerning what the initial position of variable line impedance 194 should be. Specifically, assume that at a defined constant pressure, variable line impedance has a flow rate (for chilled carbonated water 164) of between 0.00 mL/second and 120.00 mL/second. Further, assume that a flow rate of 40 mL/second is desired when filing container 30 with product 28. Accordingly, feed forward controller 354 may provide a feed forward signal (on feed forward line 384) that initially opens variable line impedance 194 to 33.33% of its maximum opening (assuming that variable line impedance 194 operates in a linear fashion).

When determining the value of the feed forward signal, feed forward controller 354 may utilize a lookup table (not shown) that may be developed empirically and may define the signal to be provided for various initial flow rates. An example of such a lookup table may include, but is not limited to, the following table:

| Flowrate $_{mL/second}$ | Signal $_{to\ stepper\ controller}$ |
|---|---|
| 0 | pulse to 0 degrees |
| 20 | pulse to 30 degrees |
| 40 | pulse to 60 degrees |
| 60 | pulse to 150 degrees |
| 80 | pulse to 240 degrees |
| 100 | pulse to 270 degrees |
| 120 | pulse to 300 degrees |

Again, assuming that a flow rate of 40 mL/second is desired when filing container 30 with product 28, feed forward controller 354 may utilize the above-described lookup table and may pulse the stepper motor to 60.0 degrees (using feed forward line 384).

Unit delay 356 may form a feedback path through which a previous version of the control signal (provided to variable line impedance 194) is provided to flow controller 352.

Saturation controller 358 may be configured to disable the integral control of feedback controller system 182 (which, as discussed above, may be configured as a PI loop controller) whenever variable line impedance 194 is set to a maximum flow rate (by stepper controller 360), thus increasing the stability of the system by reducing flow rate overshoots and system oscillations.

Stepper controller 360 may be configured to convert the signal provided by saturation controller 358 (on line 386) into a signal usable by variable line impedance 194. Variable line impedance 194 may include a stepper motor for adjusting the orifice size (and, therefore, the flow rate) of variable line impedance 194. Accordingly, control signal 188 may be configured to control the stepper motor included within variable line impedance.

Figure 6:
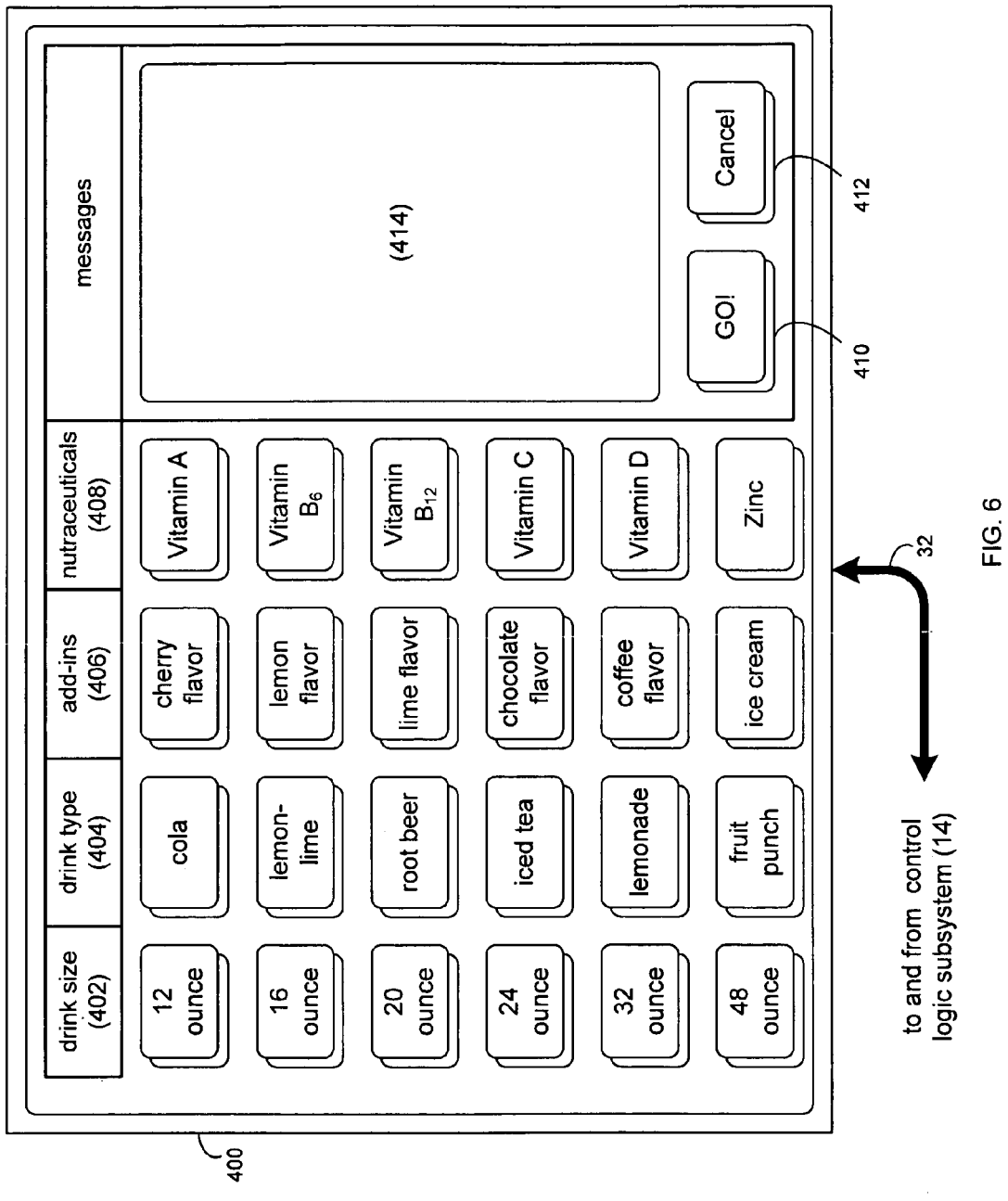
FIG. 6 is a diagrammatic view of one embodiment of a user interface subsystem included within the processing system of FIG. 1.

Referring also to FIG. 6, a diagrammatic view of user interface subsystem 22 is shown. User interface subsystem 22 may include touch screen interface 400 that allows user 26 to select various options concerning product 28. For example, user 26 (via "drink size" column 402) may be able to select the size of product 28. Examples of the selectable sizes may include but are not limited to: "12 ounce"; "16 ounce"; "20 ounce"; "24 ounce"; "32 ounce"; and "48 ounce".

User 26 may be able to select (via "drink type" column 404) the type of product 28. Examples of the selectable types may include but are not limited to: "cola"; "lemon-lime"; "root beer"; "iced tea"; "lemonade"; and "fruit punch".

User 26 may also be able to select (via "add-ins" column 406) one or more flavorings/products for inclusion within product 28. Examples of the selectable add-ins may include but are not limited to: "cherry flavor"; "lemon flavor"; "lime flavor"; "chocolate flavor"; "coffee flavor"; and "ice cream".

Further, user 26 may be able to select (via "nutraceuticals" column 408) one or more nutraceuticals for inclusion within product 28. Examples of such nutraceuticals may include but are not limited to: "Vitamin A"; "Vitamin $B_6$"; "Vitamin $B_{12}$"; "Vitamin C"; "Vitamin D"; and "Zinc".

In some embodiments, an additional screen at a level lower than the touch screen may include a "remote control" (not shown) for the screen. The remote control may include buttons indicating up, down, left and right and select, for example. However, in other embodiments, additional buttons may be included.

Once user 26 has made the appropriate selections, user 26 may select "GO!" button 410 and user interface subsystem 22 may provide the appropriate data signals (via data bus 32) to control logic subsystem 14. Once received, control logic subsystem 14 may retrieve the appropriate data from storage subsystem 12 and may provide the appropriate control signals to e.g., high volume ingredient subsystem 16, micro ingredient subsystem 18, and plumbing/control subsystem 20, which may be processed (in the manner discussed above) to prepare product 28. Alternatively, user 26 may select "Cancel" button 412 and touch screen interface 400 may be reset to a default state (e.g., no buttons selected).

User interface subsystem 22 may be configured to allow for bidirectional communication with user 26. For example, user interface subsystem 22 may include informational screen 414 that allows processing system 10 to provide information to user 26. Examples of the types of information that may be provided to user 26 may include but is not limited to advertisements, information concerning system malfunctions/warnings, and information concerning the cost of various products.

As discussed above, during use of processing system 10, user 26 may select a particular product 28 for dispensing (into container 30) using user interface subsystem 22. Via user interface subsystem 22, user 26 may select one or more options for inclusion within such beverage. Once user 26 makes the appropriate selections, via user interface subsystem 22, user interface subsystem 22 may send the appropriate data signals (via data bus 32) to control logic subsystem 14. Control logic subsystem 14 may process these data signals and may retrieve (via data bus 34) one or more recipes chosen from plurality of recipes 36 maintained on storage subsystem 12. Upon retrieving the recipe(s) from storage subsystem 12, control logic subsystem 14 may process the recipe(s) and provide the appropriate control signals (via data bus 38) to e.g. high volume ingredient subsystem 16 microingredient subsystem 18 and plumbing/control subsystem 20, resulting in the production of product 28 (which is dispensed into container 30).

When user 26 makes their selection, user 26 may select a multi-portion recipe that is essentially the combination of two separate and distinct recipes. For example, user 26 may select a root beer float, which is a multi-portion recipe that is essentially the combination of two separate and distinct recipes (i.e. vanilla ice cream and root beer soda). As a further example, user 26 may select a drink that is a combination of cola and coffee. This cola/coffee combination is essentially a combination of two separate and distinct recipes (i.e. cola soda and coffee).

Accordingly, assume that processing system 10 receives instructions (via user interface subsystem 22) to create a root beer float, knowing that a recipe for a root beer float is a multi-portion recipe, processing system 10 may simply obtain the standalone recipe for root beer soda, obtain the standalone recipe for vanilla ice cream, and execute both recipes to produce root beer soda and vanilla ice cream (respectively). Once these products are produced, processing system 10 may combine the individual products (namely root beer soda and vanilla ice cream) to produce the root beer float requested by user 26.

When executing a recipe, processing system 10 may utilize one or more manifolds (not shown) included within processing system 10. As used in this disclosure, a manifold is a temporary storage area designed to allow for the execution of one or more processes. In order to facilitate the movement of ingredients into and out of the manifolds, processing system 10 may include a plurality of valves (controllable by e.g., control logic subsystem 14) for facilitating the transfer of ingredients between manifolds. Examples of various types of manifolds may include but are not limited to: a mixing manifold, a blending manifold, a grinding manifold, a heating manifold, a cooling manifold, a freezing manifold, a steeping manifold, a nozzle, a pressure manifold, a vacuum manifold, and an agitation manifold.

For example, when making coffee, a grinding manifold may grind coffee beans. Once the beans are ground, water may be provided to a heating manifold in which water 160 is heated to a predefined temperature (e.g. 212° F.). Once the water is heated, the heated water (as produced by the heating manifold) may be filtered through the ground coffee beans (as produced by the grinding manifold). Additionally and depending on how processing system 10 is configured, processing system 10 may add cream and/or sugar to the coffee produced in another manifold or at nozzle 24.

As discussed above, control logic subsystem 14 may execute one or more control processes 120 that may control the operation of processing system 10. Accordingly, control logic subsystem 14 may execute virtual manifold process 122.

Figure 7:
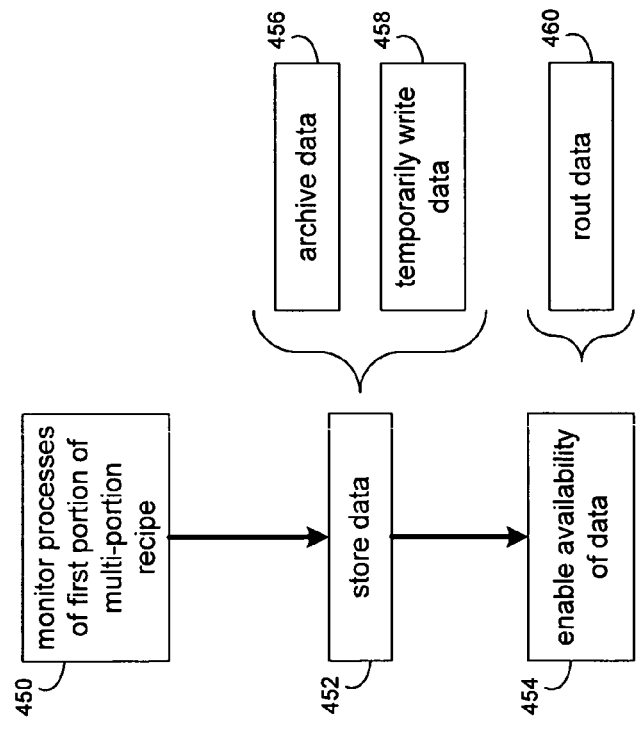
FIG. 7 is a flowchart of one embodiment of a virtual manifold process executed by the control logic subsystem of FIG. 1.

Referring also to FIG. 7, virtual manifold process 122 may monitor 450 one or more processes occurring during a first portion of a multi-portion recipe being executed on e.g., processing system 10 to obtain data concerning at least of portion of the one or more processes. For example, assume that the multi-portion recipe concerns the making of a root beer float, which (as discussed above) is essentially the combination of two separate and distinct recipes (i.e. root beer soda and vanilla ice cream) that may be chosen from plurality of recipes 36 maintained on storage subsystem 12. Accordingly, the first portion of the multi-portion recipe may be considered the one or more processes utilized by processing system 10 to make root beer soda. Further, the second portion of the multi-portion recipe may be considered the one or more processes utilized by processing system 10 to make vanilla ice cream.

Each portion of these multi-portion recipes may be executed in a different manifold included within processing system 10. For example, the first portion of the multi-portion recipe (i.e., the one or more processes utilized by processing system 10 to make root beer soda) may be executed within a mixing manifold included within processing system 10. Further, the second portion of the multi-portion recipe (i.e., the one or more processes utilized by processing system 10 to make vanilla ice cream) may be executed within a freezing manifold included within processing system 10. As discussed above, processing system 10 may include a plurality of manifolds, examples of which may include but are not limited to: mixing manifolds, blending manifolds, grinding manifolds, heating manifolds, cooling manifolds, freezing manifolds, steeping manifolds, nozzles, pressure manifolds, vacuum manifolds, and agitation manifolds.

Accordingly, virtual manifold process 122 may monitor 450 the processes utilized by processing system 10 to make root beer soda (or may monitor the processes utilized by processing system 10 to make vanilla ice cream) to obtain data concerning these processes.

Examples of the type of data obtained may include but is not limited to ingredient data and processing data.

Ingredient data may include but is not limited to a list of ingredients used during the first portion of a multi-portion recipe. For example, if the first portion of a multi-portion recipe concerns making root beer soda, the list of ingredients may include: a defined quantity of root beer syrup, a defined quantity of carbonated water, a defined quantity of non-carbonated water, and a defined quantity of high fructose corn syrup.

Processing data may include but is not limited to a sequential list of processes performed on the ingredients. For example, a defined quantity of carbonated water may begin to be introduced into a manifold within processing system 10. While filling the manifold with carbonated water, the defined quantity of root beer syrup, the defined quantity of high fructose corn syrup, and the defined quantity of non-carbonated water may also be introduced into the manifold.

At least a portion of the data obtain may be stored 452 (e.g., either temporarily or permanently). Further, virtual manifold process 122 may enable 454 the availability of this stored data for subsequent use by e.g., one or more processes occurring during a second portion of the multi-portion recipe. When storing 452 the data obtained, virtual manifold process 122 may archive 456 the data obtained in a nonvolatile memory system (e.g., storage subsystem 12) for subsequent diagnostic purposes. Examples of such diagnostic purposes may include enabling a service representative/customer representative to review ingredient consumption characteristics to establish a purchasing plan for purchasing consumables for processing system 10. Alternatively/additionally, when storing 452 the data obtained, virtual manifold process 122 may temporarily write the data obtained to a volatile memory system (e.g., random access memory 104).

When enabling 454 the availability of the data obtained, virtual manifold process 122 may rout 460 the obtained data (or a portion thereof) to one or more processes that are occurring (or will occur) during the second portion of the multi-portion recipe. Continuing with the above-stated example, in which the second portion of the multi-portion recipe concerns the one or more processes utilized by processing system 10 to make vanilla ice cream, virtual manifold process 122 may enable 454 the data obtained (or a portion thereof) to be available to the one or more processes utilized to make vanilla ice cream.

Assume that the root beer syrup utilized to make the above-described root beer float is flavored with a considerable quantity of vanilla flavoring. Further, assume that when making the vanilla ice cream, a considerable quantity of vanilla flavoring is also used. As virtual manifold process 122 may enable 454 the availability of the obtained data (e.g., ingredient and/or process data) to control logic subsystem (i.e., the subsystem orchestrating the one or more processes utilized to make the vanilla ice cream), upon reviewing this data, control logic subsystem 14 may alter the ingredients utilized to make the vanilla ice cream. Specifically, control logic subsystem 14 may reduce the quantity of vanilla flavoring utilized to make the vanilla ice cream to avoid an overabundance of vanilla flavoring within the root beer float.

Additionally, by enabling the availability of the obtained data to subsequently-executed processes, procedures may be performed that would prove impossible had that data not been made available to the subsequently-executed processes. Continuing with the above-stated example, assume that it is determined empirically that consumers tend to not like any single-serving of a product that includes more than 10.0 mL of vanilla flavoring. Further, assume that 8.0 mL of vanilla flavoring is included within the root beer syrup utilized to make the root beer soda for the root beer float, and another 8.0 mL of vanilla flavoring is utilized to make the vanilla ice cream utilized to make the root beer float. Therefore, if these two products (the root beer soda and the vanilla ice cream) are combined, the final product would be flavored with 16.0 mL of vanilla flavoring (which exceeds the empirically-defined not-to-exceed 10.0 mL rule).

Accordingly, if the ingredient data for the root beer soda was not stored 452 and the availability of such stored data was not enabled 454 by virtual manifold process 122, the fact that the root beer soda contains 8.0 mL of vanilla flavoring would be lost and a final product containing 16.0 mL of vanilla flavoring would be produced. Accordingly, this obtained and stored 452 data may be utilized to avoid (or reduce) the occurrence of any undesirable effect (e.g., an undesired flavor characteristic, an undesired appearance characteristic, an undesired odor characteristic, an undesired texture characteristic, and exceeding a maximum recommended dosage of a nutraceutical).

The availability of this obtained data may allow for subsequent processes to also be adjusted. For example, assume that the quantity of salt utilized to make the vanilla ice cream varies depending on the quantity of carbonated water utilized to make the root beer soda. Again, if the ingredient data for the root beer soda was not stored 452 and the availability of such stored data was not enabled 454 by virtual manifold process 122, the quantity of carbonated water used to make the root beer soda would be lost and the ability to adjust the quantity of salt utilized to make the ice cream may be compromised.

As discussed above, virtual manifold process 122 may monitor 450 one or more processes occurring during a first portion of a multi-portion recipe being executed on e.g., processing system 10 to obtain data concerning at least of portion of the one or more processes. The one or more processes monitored 450 may be executed within a single manifold of the processing system 10 or may be representative of a single portion of a multi-portion procedure executed within a single manifold of processing system 10.

For example, when making the root beer soda, a single manifold may be used that has four inlets (e.g., one for the root beer syrup, one for the carbonated water, one for the non-carbonated water, and one for the high fructose corn syrup) and one outlet (as all of the root beer soda is being provided to a single secondary manifold).

However, if instead of having one outlet, the manifold has two outlets (one having a flow rate of four times the other), virtual manifold process 122 may consider this process to include two separate and distinct portions being executed simultaneously within the same manifold. For example, 80% of all of the ingredients may be mixed together to produce 80% of the total quantity of root beer soda; while the remaining 20% of all of the ingredients may be simultaneously mixed together (in the same manifold) to produce 20% of the root beer soda. Accordingly, virtual manifold process 122 may enable 454 the data obtained concerning the first portion (i.e., the 80% portion) to be made available to the downstream process that utilizes the 80% of the root beer soda and enable 454 the data obtained concerning the second portion (i.e., the 20% portion) to be made available to the downstream process that utilizes the 20% of the root beer soda.

Additionally/alternatively, the single portion of a multi-portion procedure executed within a single manifold of processing system 10 may be indicative of one process that occurs within a single manifold that executes a plurality of discrete processes. For example, when making vanilla ice cream within the freezing manifold, the individual ingredients may be introduced, mixed, and reduced in temperature until frozen. Accordingly, the process of making vanilla ice cream may include an ingredient introduction process, an ingredient mixing process, and an ingredient freezing process, each of which may be individually monitored 450 by virtual manifold process 122.

As discussed above, control logic subsystem 14 may execute one or more control processes 120 that may control the operation of processing system 10. Accordingly, control logic subsystem 14 may execute virtual machine process 124.

As also discussed above, during use of processing system 10, user 26 may select a particular product 28 for dispensing (into container 30) using user interface subsystem 22. Via user interface subsystem 22, user 26 may select one or more options for inclusion within such beverage. Once user 26 makes the appropriate selections, via user interface subsystem 22, user interface subsystem 22 may send the appropriate indication to control logic subsystem 14, indicating the selections and preferences of user 26 (with respect to product 28).

When making a selection, user 26 may select a multi-portion recipe that is essentially the combination of two separate and distinct recipes that produces a multi-component product. For example, user 26 may select a root beer float, which is a multi-portion recipe that is essentially the combination of two separate and distinct components (i.e. vanilla ice cream and root beer soda). As a further example, user 26 may select a drink that is a combination of cola and coffee. This cola/coffee combination is essentially a combination of two separate and distinct components (i.e. cola soda and coffee).

Figure 8:
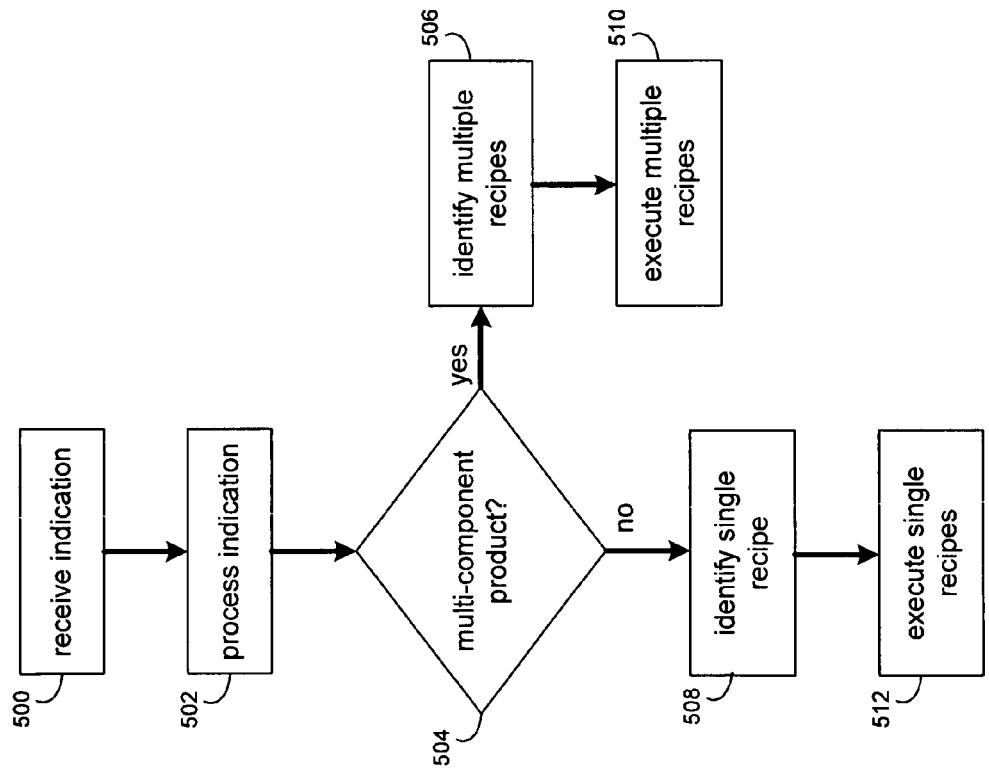
FIG. 8 is a flowchart of one embodiment of a virtual machine process executed by the control logic subsystem of FIG. 1.

Referring also to FIG. 8, upon receiving 500 the above-described indication, virtual machine process 124 may process 502 this indication to determine if the product to be produced (e.g., product 28) is a multi-component product.

If 504 the product to be produced is a multi-component product, virtual machine process 124 may identify 506 a first recipe for producing a first component of the multi-component product and at least a second recipe for producing at least a second component of the multi-component product. The first and second recipes may be chosen from plurality of recipes 36 maintained on storage subsystem 12.

If 504 the product to be produced is not a multi-component product, virtual machine process 124 may identify 508 a single recipe for producing the product. The single recipe may be chosen from plurality of recipes 36 maintained on storage subsystem 12. Accordingly, if the indication received 500 was an indication concerning a lemon-lime soda, as this is not a multi-component product, virtual machine process may identify 508 the single recipe required to produce the lemon-lime soda.

Upon identifying 506, 508 the recipe(s) from plurality of recipes 36 maintained on storage subsystem 12, control logic subsystem 14 may execute 510, 512 the recipe(s) and provide the appropriate control signals (via data bus 38) to e.g. high volume ingredient subsystem 16 microingredient subsystem 18 and plumbing/control subsystem 20, resulting in the production of product 28 (which is dispensed into container 30).

Accordingly, assume that processing system 10 receives an indication (via user interface subsystem 22) to create a root beer float. Virtual machine process 124 may process 502 this indication to determine if 504 the root beer float is a multi-component product. As the root beer float is a multi-component product, virtual machine process 124 may identify 506 the recipes required to produce the root beer float (namely the recipe for root beer soda and the recipe for vanilla ice cream) and execute 510 both recipes to produce root beer soda and vanilla ice cream (respectively). Once these products are produced, processing system 10 may combine the individual products (namely root beer soda and vanilla ice cream) to produce the root beer float requested by user 26.

As discussed above, control logic subsystem 14 may execute one or more control processes 120 that may control the operation of processing system 10. Accordingly, control logic subsystem 14 may execute FSM (i.e., finite state machine) process 126.

As also discussed above, during use of processing system 10, user 26 may select a particular product 28 for dispensing (into container 30) using user interface subsystem 22. Via user interface subsystem 22, user 26 may select one or more options for inclusion within such beverage. Once user 26 makes the appropriate selections, via user interface subsystem 22, user interface subsystem 22 may send the appropriate indication to control logic subsystem 14, indicating the selections and preferences of user 26 (with respect to product 28). Again, the selection made by the user may be indicative of a multi-component product.

Figure 9:
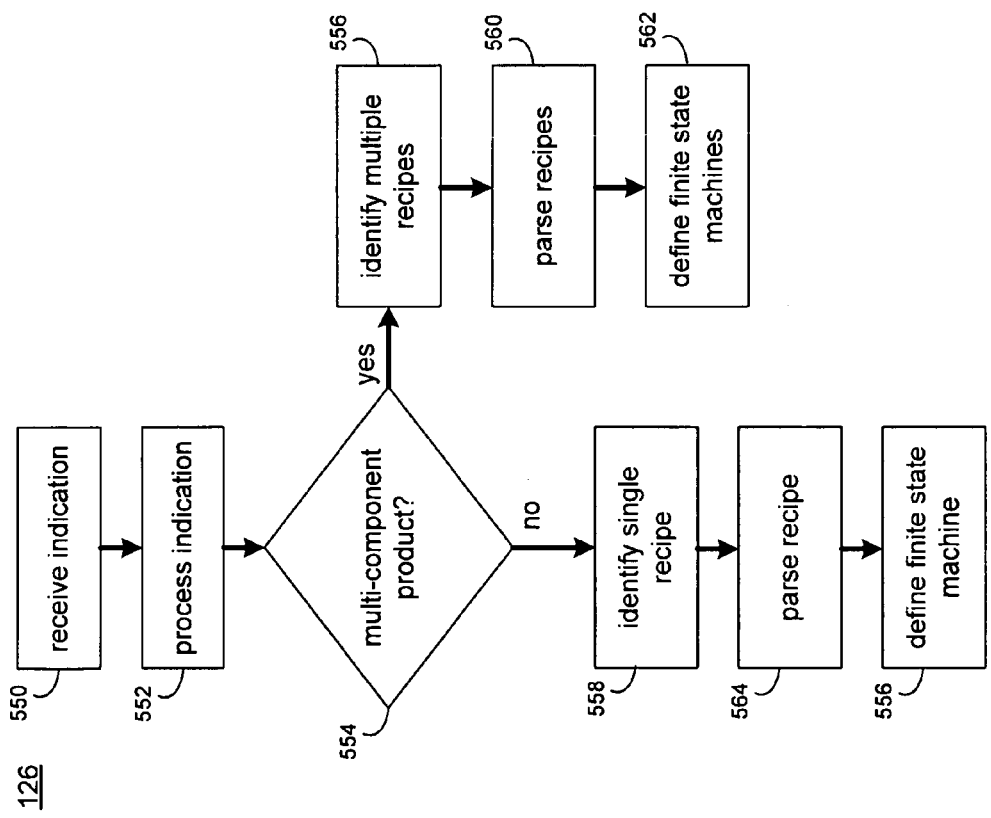
FIG. 9 is a flowchart of one embodiment of an FSM process executed by the control logic subsystem of FIG. 1.

Referring also to FIG. 9, upon receiving 550 the above-described indication, FSM process 126 may process 552 the indication to determine if the product to be produced (e.g., product 28) is a multi-component product.

If 554 the product to be produced is a multi-component product, FSM process 126 may identify 556 the recipe(s) required to produce each of the components of the multi-component product. The recipe(s) identified may be chosen from plurality of recipes 36 maintained on storage subsystem 12.

If 554 the product to be produced is not a multi-component product, FSM process 126 may identify 558 a single recipe for producing the product. The single recipe may be chosen from plurality of recipes 36 maintained on storage subsystem 12. Accordingly, if the indication received 550 and processed 552 was an indication that defined a lemon-lime soda, as this is not a multi-component product, FSM process 126 may identify 558 the single recipe required to produce the lemon-lime soda.

If 554 the indication concerns a multi-component product, upon identifying 556 the appropriate recipes chosen from plurality of recipes 36 maintained on storage subsystem 12, FSM process 126 may parse 560 each of the recipes into a plurality of discrete states and define one or more state transitions. FSM process 126 may then define 562 at least one finite state machine (for each recipe) using at least a portion of the plurality of discrete states.

If 554 the indication does not concern a multi-component product, upon identifying 558 the appropriate recipe chosen from plurality of recipes 36 maintained on storage subsystem 12, FSM process 126 may parse 564 the recipe into a plurality of discrete states and define one or more state transitions. FSM process 126 may then define 566 at least one finite state machine for the recipe using at least a portion of the plurality of discrete states.

Figure 10:
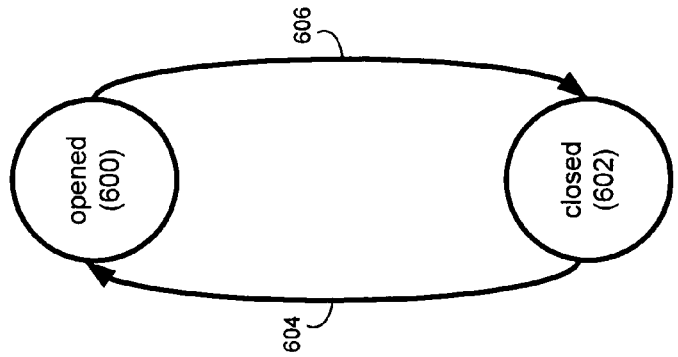
FIG. 10 is a diagrammatic view of one embodiment of a first state diagram.

As is known in the art, a finite state machine (FSM) is a model of behavior composed of a finite number of states, transitions between those states and/or actions. For example and referring also to FIG. 10, if defining a finite state machine for a physical doorway that can either be fully opened or fully closed, the finite state machine may include two states, namely "opened" state 600 and "closed" state 602. Additionally, two transitions may be defined that allow for the transition from one state to another state. For example, transition state 604 "opens" the door (thus transitioning from "closed" state 602 to "open" state 600) and transition state 606 "closes" the door (thus transitioning from "opened" state 600 to "closed" state 602).

Figure 11:
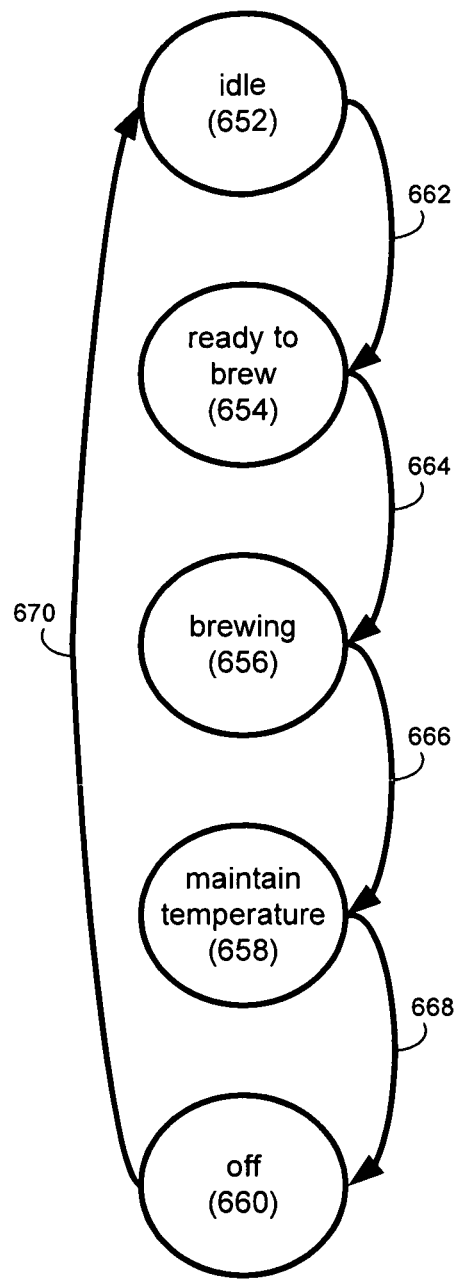
FIG. 11 is a diagrammatic view of one embodiment of a second state diagram.

Referring also to FIG. 11, a state diagram 650 concerning the manner in which coffee may be brewed is shown. State diagram 650 is shown to include five states, namely: idle state 652; ready to brew state 654; brewing state 656; maintain temperature state 658; and off state 660. Additionally, five transition states are shown. For example, transition state 662 (e.g., installing coffee filter, installing coffee grounds, filling coffee machine with water) may transition from idle state 652 to ready to brew state 654. Transition state 664 (e.g., pressing the brew button) may transition from ready to brew state 654 to brewing state 656. Transition state 666 (e.g., exhausting the water supply) may transition from brewing state 656 to maintain temperature 658. Transition state 668 (e.g., turning the power switch off or exceeding a maximum "maintain temperature" time) may transition from maintain temperature state 658 to off state 660. Transition state 670 (e.g., turning the power switch on) may transition from off state 660 to idle state 652.

Accordingly, FSM process 126 may generate one or more finite state machines that correspond to the recipes (or portions thereof) utilized to produce a product. Once the appropriate finite state machines are produced, control logic subsystem 14 may execute the finite state machine(s) and generate the product (e.g., multi-component or single component) requested by e.g., user 26.

Accordingly, assume that processing system 10 receives 650 an indication (via user interface subsystem 22) that user 26 has selected a root beer float. FSM process 126 may process 652 the indication to determine if 654 the root beer float is a multi-component product. As the root beer float is a multi-component product, FSM process 126 may identify 656 the recipes required to produce the root beer float (namely the recipe for root beer soda and the recipe for vanilla ice cream) and parse 660 the recipe for root beer soda and the recipe for vanilla ice cream into a plurality of discrete states and define one or more state transitions. FSM process 126 may then define 662 at least one finite state machine (for each recipe) using at least a portion of the plurality of discrete states. These finite state machines may subsequently be executed by control logic subsystem 14 to produce the root beer float selected by user 26. When executing the state machines corresponding to the recipes, processing system 10 may utilize one or more manifolds (not shown) included within processing system 10.

While the various electrical components, mechanical components, electromechanical components, and software processes are described above as being utilized within a processing system that dispenses beverages, this is for illustrative purposes only and is not intended to be a limitation of this disclosure, as other configurations are possible. For example, the above-described processing system may be utilized for processing/dispensing other consumable products (e.g., ice cream and alcoholic drinks). Additionally, the above-described system may be utilized in areas outside of the food industry. For example, the above-described system may be utilized for processing/dispensing: vitamins; pharmaceuticals; medical products, cleaning products; lubricants; painting/staining products; and other non-consumable liquids/semi-liquids/granular solids and/or fluids.

As discussed above, the various electrical components, mechanical components, electromechanical components, and software processes of processing system 10 generally (and virtual manifold process 122, virtual machine process 124, and FSM process 126 specifically) may be used in any machine in which on-demand creation of a product from one or more substrates (also referred to as "ingredients") is desired.

In the various embodiments, the product is created following a recipe that is programmed into the processor. As discussed above, the recipe may be updated, imported or changed by permission. A recipe may be requested by a user, or may be preprogrammed to be prepared on a schedule. The recipes may include any number of substrates or ingredients and the product generated may include any number of substrates or ingredients in any concentration desired.

The substrates used may be any fluid, at any concentration, or, any powder or other solid that may be reconstituted either while the machine is creating the product or before the machine creates the product (i.e., a "batch" of the reconstituted powder or solid may be prepared at a specified time in preparation for metering to create additional products or dispensing the "batch" solution as a product). In various embodiments, two or more substrates may themselves be mixed in one manifold, and then metered to another manifold to mix with additional substrates.

Thus, in various embodiments, on demand, or prior to actual demand but at a desired time, a first manifold of a solution may be created by metering into the manifold, according to the recipe, a first substrate and at least one additional substrate. In some embodiments, one of the substrates may be reconstituted, i.e., the substrate may be a powder/solid, a particular amount of which is added to a mixing manifold. A liquid substrate may also be added to the same mixing manifold and the powder substrate may be reconstituted in the liquid to a desired concentration. The contents of this manifold may then be provided to e.g., another manifold or dispensed.

In some embodiments, the methods described herein may be used in conjunction with mixing on-demand dialysate, for use with peritoneal dialysis or hemodialysis, according to a recipe/prescription. As is known in the art, the composition of dialysate may include, but is not limited to, one or more of the following: bicarbonate, sodium, calcium, potassium, chloride, dextrose, lactate, acetic acid, acetate, magnesium, glucose and hydrochloric acid.

The dialysate may be used to draw waste molecules (e.g., urea, creatinine, ions such as potassium, phosphate, etc.) and water from the blood into the dialysate through osmosis, and dialysate solutions are well-known to those of ordinary skill in the art.

For example, a dialysate typically contains various ions such as potassium and calcium that are similar to their natural concentration in healthy blood. In some cases, the dialysate may contain sodium bicarbonate, which is usually at a concentration somewhat higher than found in normal blood. Typically, the dialysate is prepared by mixing water from a source of water (e.g., reverse osmosis or "RO" water) with one or more ingredients: an "acid" (which may contain various species such as acetic acid, dextrose, NaCl, CaCl, KCl, MgCl, etc.), sodium bicarbonate ($NaHCO_3$), and/or sodium chloride (NaCl). The preparation of dialysate, including using the appropriate concentrations of salts, osmolarity, pH, and the like, is also well-known to those of ordinary skill in the art. As discussed in detail below, the dialysate need not be prepared in real-time, on-demand. For instance, the dialysate can be made concurrently or prior to dialysis, and stored within a dialysate storage vessel or the like.

In some embodiments, one or more substrates, for example, the bicarbonate, may be stored in powder form. Although for illustrative and exemplary purposes only, a powder substrate may be referred to in this example as "bicarbonate", in other embodiments, any substrate/ingredient, in addition to, or instead of, bicarbonate, may be stored in a machine in powder form or as another solid and the process described herein for reconstitution of the substrate may be used. The bicarbonate may be stored in a "single use" container that, for example, may empty into a manifold. In some embodiments, a volume of bicarbonate may be stored in a container and a particular volume of bicarbonate from the container may be metered into a manifold. In some embodiments, the entire volume of bicarbonate may be completely emptied into a manifold, i.e., to mix a large volume of dialysate.

The solution in the first manifold may be mixed in a second manifold with one or more additional substrates/ingredients. In addition, in some embodiments, one or more sensors (e.g., one or more conductivity sensors) may be located such that the solution mixed in the first manifold may be tested to ensure the intended concentration has been reached. In some embodiments, the data from the one or more sensors may be used in a feedback control loop to correct for errors in the solution. For example, if the sensor data indicates the bicarbonate solution has a concentration that is greater or less than the desired concentration, additional bicarbonate or RO may be added to the manifold.

In some recipes in some embodiments, one or more ingredients may be reconstituted in a manifold prior to being mixed in another manifold with one or more ingredients, whether those ingredients are also reconstituted powders/solids or liquids.

Thus, the system and methods described herein may provide a means for accurate, on-demand production or compounding of dialysate, or other solutions, including other solutions used for medical treatments. In some embodiments, this system may be incorporated into a dialysis machine, such as those described in U.S. patent application Ser. No. 12/072,908 filed on 27 Feb. 2008 and having a priority date of 27 Feb. 2007, which is herein incorporated by reference in its entirety. In other embodiments, this system may be incorporated into any machine where mixing a product, on-demand, may be desired.

Water may account for the greatest volume in dialysate, thus leading to high costs, space and time in transporting bags of dialysate. The above-described processing system 10 may prepare the dialysate in a dialysis machine, or, in a standalone dispensing machine (e.g., on-site at a patient's home), thus eliminating the need for shipping and storing large numbers of bags of dialysate. This above-described processing system 10 may provide a user or provider with the ability to enter the prescription desired and the above-described system may, using the systems and methods described herein, produce the desired prescription on-demand and on-site (e.g., including but not limited to: a medical treatment center, pharmacy or a patient's home). Accordingly, the systems and methods described herein may reduce transportation costs as the substrates/ingredients are the only ingredient requiring shipping/delivery.

As discussed above, other examples of such products producible by processing system 10 may include but are not limited to: dairy-based products (e.g., milkshakes, floats, malts, frappes); coffee-based products (e.g., coffee, cappuccino, espresso); soda-based products (e.g., floats, soda w/fruit juice); tea-based products (e.g., iced tea, sweet tea, hot tea); water-based products (e.g., spring water, flavored spring water, spring water w/vitamins, high-electrolyte drinks, high-carbohydrate drinks); solid-based products (e.g., trail mix, granola-based products, mixed nuts, cereal products, mixed grain products); medicinal products (e.g., infusible medicants, injectable medicants, ingestible medicants); alcohol-based products (e.g., mixed drinks, wine spritzers, soda-based alcoholic drinks, water-based alcoholic drinks); industrial products (e.g., solvents, paints, lubricants, stains); and health/beauty aid products (e.g., shampoos, cosmetics, soaps, hair conditioners, skin treatments, topical ointments).

A number of implementations have been described. Nevertheless, it will be understood that various modifications may be made. Accordingly, other implementations are within the scope of the following claims.

What is claimed is:

1. A method comprising:
receiving instructions to generate a multi-component product on a processing device;
processing the instructions;
identifying a first recipe to produce a first component of the multi-component product;
identifying at least a second recipe to produce at least a second component of the multi-component product, wherein the first and second recipes are chosen from a plurality of available recipes;
altering the first recipe based on the second recipe; and
executing the first and second recipes,
wherein the first recipe is executed within a first manifold of the processing device, wherein the first manifold is chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold, and
wherein the second recipe is executed within a second manifold of the processing device, wherein the second manifold is different from the first manifold, and wherein the second manifold is chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

2. A computer program product residing on a non-transitory computer readable medium having a plurality of instructions stored thereon which, when executed by a processor, cause the processor to perform operations comprising:
receiving instructions to generate a multi-component product on a processing device;
processing the instructions;
identifying a first recipe to produce a first component of the multi-component product;
identifying at least a second recipe to produce at least a second component of the multi-component product, wherein the first and second recipes are chosen from a plurality of available recipes;
altering the first recipe based on the second recipe; and
executing the first and second recipes,
wherein the first recipe is executed within a first manifold of the processing device, wherein the first manifold is chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold, and
wherein the second recipe is executed within a second manifold of the processing device, wherein the second manifold is different from the first manifold, and wherein the second manifold is chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

3. A process controller configured to:
receive instructions to generate a multi-component product on a processing device;
process the instructions;
identify a first recipe to produce a first component of the multi-component product;
identify at least a second recipe to produce at least a second component of the multi-component product, wherein the first and second recipes are chosen from a plurality of available recipes;
altering the first recipe based on the second recipe; and
execute the first and second recipes,
wherein the first recipe is executed within a first manifold of the processing device, wherein the first manifold is chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold, and
wherein the second recipe is executed within a second manifold of the processing device, wherein the second manifold is different from the first manifold, and wherein the second manifold is chosen from the group consisting of: a mixing manifold, a blending manifold, a grinding manifold, a heating manifold, a cooling manifold, a freezing manifold, a steeping manifold, a nozzle, a pressure manifold, a vacuum manifold, and an agitation manifold.

* * * * *